United States Patent [19]

Moring

[11] Patent Number: 5,274,227
[45] Date of Patent: Dec. 28, 1993

[54] CAPILLARY DETECTOR CELL HAVING IMAGING ELEMENTS POSITIONED TO OPTIMIZE SENSITIVITY

[75] Inventor: Stephen E. Moring, San Mateo, Calif.
[73] Assignee: Applied Biosystems, Inc., Foster City, Calif.
[21] Appl. No.: 965,827
[22] Filed: Oct. 23, 1992
[51] Int. Cl.⁵ .................................................. H01J 5/16
[52] U.S. Cl. ......................... 250/227.25; 73/61.53; 356/411; 385/32
[58] Field of Search ............... 250/227.14, 227.23, 250/227.20, 227.24, 22.25; 73/61.52, 61.53, 61.58; 356/410, 411, 432, 246; 385/32, 48

[56] References Cited

U.S. PATENT DOCUMENTS

| | | | |
|---|---|---|---|
| 4,747,652 | 5/1988 | Campbell et al. | 385/32 |
| 4,747,687 | 5/1988 | Hoppe et al. | 356/410 |
| 4,834,534 | 5/1989 | Wiget | 356/410 |
| 4,856,864 | 8/1989 | Campbell | 250/227.24 |
| 5,057,216 | 10/1991 | Chervet | 210/198 |
| 5,073,345 | 12/1991 | Scott et al. | 356/411 |
| 5,239,360 | 8/1993 | Moring | 356/344 |

OTHER PUBLICATIONS

J. P. Chervet, et al, *Ultra-Sensitive UV Detection in Micro Separation*, Instrumentation, May 1989, pp. 278-281.

Alfredo E. Bruno et al, *On-Column Capillary Flow Cell Utilizing Optical . . .*, Annal Chem, 1989, 61, pp. 876-883.

*Primary Examiner*—David C. Nelms
*Assistant Examiner*—S. B. Allen
*Attorney, Agent, or Firm*—John A. Frazzini; Joseph H. Smith

[57] ABSTRACT

A detector cell, having a capillary entrance elbow through which a beam of exposing light can be directed into the bore of a central leg of the detector cell capillary. Ray traces, to determine the effect of the entrance elbow on the beam of exposing light are used to optimize performance of this detector cell. Back ray tracing is implemented to illustrate an optimized embodiment. Forward ray tracing is also illustrated and can be used to determine system performance for a range or choices of a single parameter or for concurrent ranges of choices of a subset of the parameters of the beam of exposing light.

22 Claims, 7 Drawing Sheets

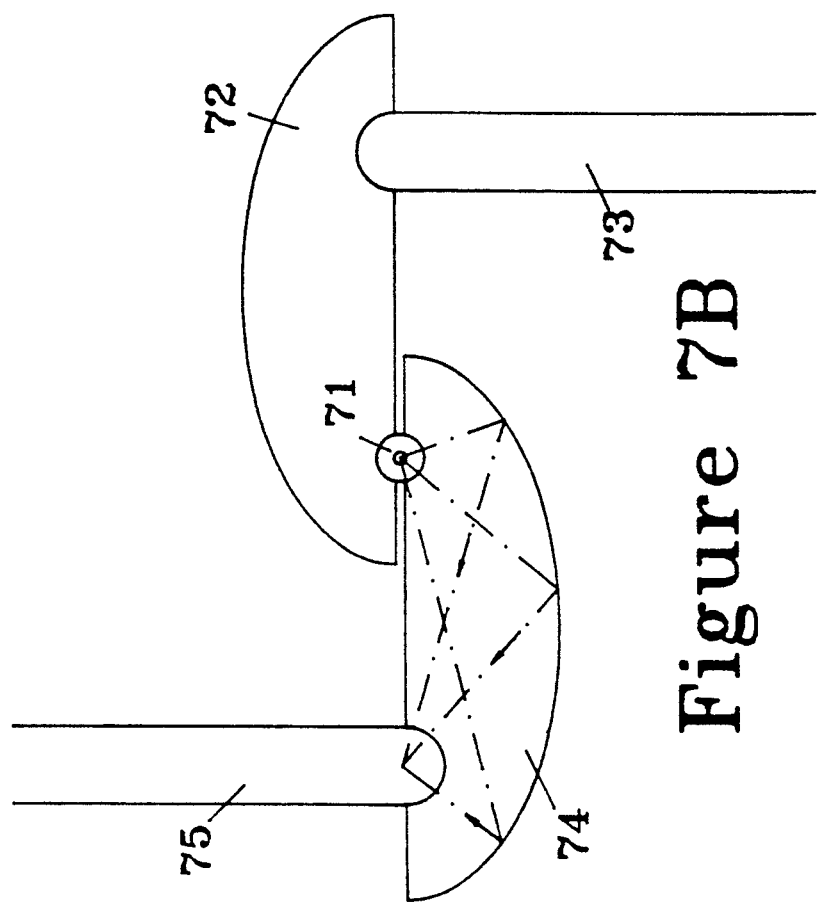
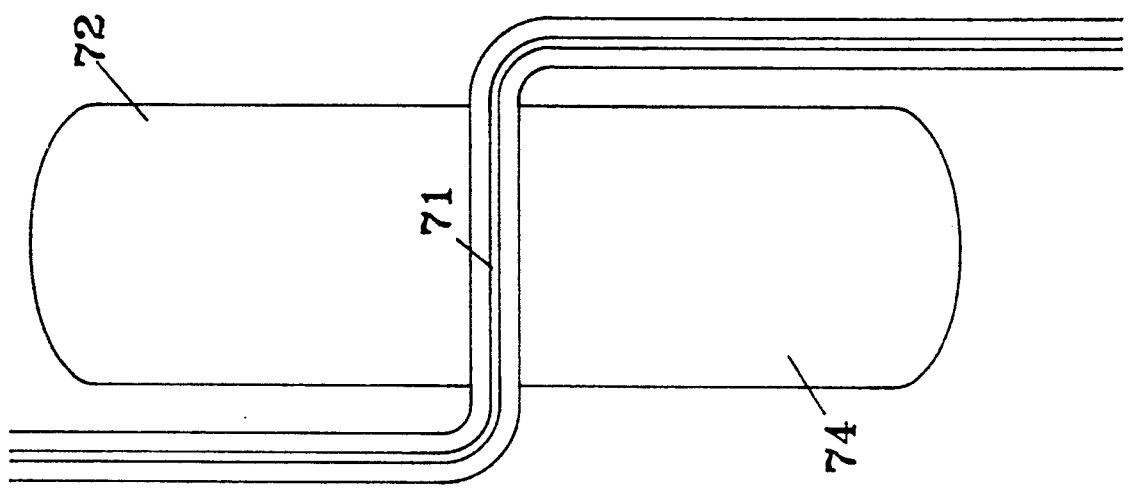
Figure 7B
Figure 7A

CAPILLARY DETECTOR CELL HAVING IMAGING ELEMENTS POSITIONED TO OPTIMIZE SENSITIVITY

TECHNICAL FIELD OF THE INVENTION

This invention relates in general to capillary detector cells and more particularly to a Z-Cell type of capillary detector cell exhibiting improved sensitivity.

CONVENTION REGARDING REFERENCE NUMERALS

In the figures, the first digit of a reference numeral indicates the first figure in which is presented the element indicated by that reference numeral. If an element is illustrated in more than one figure, then the same reference numeral will be used to identify that element in each such figure.

BACKGROUND OF THE INVENTION

Chromatographic methods are commonly used to separate a mixture into various components, so that these components can be identified and quantified. A variety of mechanisms are utilized to produce the desired separation between the components of the mixture. In one class of systems, the wall of the tube through which the mixture flows is coated with a material that exhibits different affinities for different components of the mixture. The speed of migration along the channel is greater for components exhibiting a weaker affinity for the wall, thereby producing a separation of mixture components according to their affinity for the coated wall. In another class of systems, the column is packed with a material, such as a gel or particulate, that provides the differential interaction with the components of the mixture.

These separation columns typically pass the sample solution past a detector that measures some physical property of the components, such as the light absorbance, the fluorescence emission, the refractive index or the electrical conductivity of the sample. In each of the first three of these particular cases, a light beam is passed through the sample. For the case of absorbance measurements in a capillary column, a detector is positioned adjacent to the capillary and opposite to a light source on an optical axis perpendicular to the capillary, such that the detector receives light after it passes through the sample. Fluorescence detection exhibits the advantages of superior selectivity and sensitivity in detection of many compounds.

Because absorbance and fluorescence signals are typically relatively weak, it is important to understand the fluorescent and non-fluorescent light distributions in order to maximize a performance parameter of the system, such as the signal-to-noise ratio ("S/N ratio"), the gain of the detected signal, some combination of these two signals (e.g., the minimum detectable concentration) or some other performance parameter appropriate for optimizing the system. The gain is defined to be equal to dS/dC, where S is the amplitude of the detector signal and C is the concentration of the sample. The minimum detectable concentration (MDC) is the minimum concentration that can be detected by the system and is defined to occur at that concentration for which the signal S is twice the noise signal of the system. The MDC is determined by plotting the signal S as a function of concentration and determining the concentration at which this curve has a signal value equal to twice the noise.

In the fluorescent systems presented in the article On-Column Capillary Flow Cell Utilizing Optical Waveguides For Chromatographic Applications by Alfredo E. Bruno, et al, *Anal. Chem.* 1989, 61, p. 876-883, optical fibers are utilized to carry incoherent light to the flowcell and are also utilized to transmit light to a detector. For a capillary of specified inner and outer diameters, a ray path calculation is presented that calculates the distribution of scattered light and the fraction of incident light that actually passes through the bore of the capillary. Because there is no focussing of the light from the light from the optical fiber onto the collecting optical fiber, the collection efficiency of the collecting optical fiber is limited by its acceptance angle and the spacing between the output end of the exposing optical fiber and the input end of this collecting optical fiber. Typically, each of these fluorescent systems collects less than one-eighth of the fluorescent light emitted from that system.

Because the use of small diameter bore capillaries improves the separation between the components of a sample, capillary liquid chromatography uses columns with very small internal diameters (typically 5 to 300 microns). The use of a small inner diameter capillary is also advantageous, because it reduces the amount of sample that is needed to fill the capillary during a measurement. Unfortunately, because the optical beam is typically directed substantially perpendicular to a central axis of the capillary, such reduced inner diameter also reduces the pathlength of the light through the sample, thereby degrading the signal-to-noise ratio of such measurements.

The S/N ratio has been improved by use of stronger light sources and/or coherent light sources in which the energy is concentrated at a wavelength that is particularly efficient at producing fluorescence. This improvement therefore arises from an increased amplitude of the signal. However, part of the noise component, such as scattered light, is proportional to the intensity of the exposing light. Therefore, when this portion of noise is a significant fraction of the total noise, it is important to minimize this noise component, because in such cases the signal-to-noise ratio cannot be significantly improved by use of a more intense beam of exposing light. This is particularly true for fluorescence measurements, because of the low signal level typically encountered in fluorescence measurements. It is therefore advantageous to increase the pathlength of the beam of light through the sample in order to increase the sensitivity of the system.

In the flow cell presented in U.S. Pat. No. 5,057,216, entitled Capillary Flow Cell, issued to Jean-Pierre Chervet on Oct. 14, 1991, the capillary is bent into the shape of a Z to enable a beam of exposing light to be directed along the central leg of this Z-shape, thereby increasing the pathlength from the inner diameter of the capillary to the length of this central leg of the Z-shaped capillary. A flowcell in which a portion of the capillary is bent into the shape of a Z will be referred to herein as a "Z-Cell". In a Z-Cell, the capillary has a first bend, referred to herein as the "entrance elbow" of the Z-Cell, through which some of the beam of exposing light can be passed into a straight section of the capillary and then out of a second bend, referred to herein as the "exit elbow" of the Z-Cell. The straight section of the capillary between these two elbows is referred to herein as the "central leg" of the Z-Cell. The protective coating is removed from this capillary in the elbow regions to enable this light to pass into and out of the capillary flow cell. The increased pathlength of the light through the sample should produce a corresponding increase in the sensitivity of this detection system.

Although this patent indicates that a sensitivity enhancement of at least 100 should result for this detection system in comparison to the traditional capillary detection system in which the incident light beam is perpendicular to the axis of the capillary, actual measurements of the sensitivity show that the sensitivity enhancement is closer to 4.5. Therefore, this approximately 20-fold shortfall in sensitivity from that which would be expected indicates that the exposing light is not concentrated into the bore of the capillary, but that, instead, effectively only about 5% of this beam passes through the bore in the central leg of the Z-Cell. This not only substantially offsets the sensitivity gain due to the increased pathlength, it also contributes to the noise component, because of the increased fraction of the incident beam that does not pass through the central leg can contribute to the noise component of the measured signal, but does not contribute to the signal component.

As discussed in the next section, this occurs because there does not appear to be any recognition of the effect of the entrance elbow on the incident beam of exposing light and the resulting detector response. In order to maximize the amount of light energy in the cell, at least one and preferably all of the following parameters of the beam be selected to maximize the product of the intensity and average pathlength of the exposing light through the central leg of the capillary: the diameter of the beam at the entrance elbow of the capillary; the direction of incidence of this beam on the entrance elbow relative to the axis of the central leg of the capillary; the amount of lateral offset of this beam, relative to the central leg of the capillary, at the point of incidence of the beam on the capillary; the degree of collimation of this beam at the entrance elbow; and the radius of curvature of the entrance elbow.

SUMMARY OF THE INVENTION

A capillary detector cell is presented having a capillary that includes an entrance elbow through which exposing light can be directed by an imaging system along the central axis of a central leg of this capillary detector cell, thereby enabling a beam of exposing light to travel through a "test solution" (e.g., sample or reference) within this capillary detector cell over a length much longer than the inner diameter of this capillary. In an embodiment utilized for absorbance detection, this increased pathlength through the sample likewise increases the amount of light absorption that occurs during passage through the capillary bore. In an embodiment utilized for fluorescent detection, such increased pathlength through the sample greatly increases the amount of fluorescent light that is emitted from such a sample.

The capillary detector cell preferably includes a pair of elbows (i.e., has the form of a Z-Cell), so that light can be directed by the imaging system through the entrance elbow of the Z-Cell, such that the light is centered on and parallel to the axis of the central leg of the Z-Cell and so that the light exits through an exit elbow to a detector. In an alternate embodiment, the capillary detector cell can include an in-line detector, so that no exit elbow is required to enable the light to reach the detector after passing through the sample solution.

In accordance with the illustrated preferred embodiment, a capillary detector cell is presented in which, by optimizing one or more parameters, an imaging system produces an imaged beam of exposing light that is concentrated within the bore of a central leg of a bent capillary and which is directed approximately parallel to the axis of the capillary. These parameters include: the diameter of the beam at the entrance elbow of the capillary; the direction of incidence of this beam on the entrance elbow relative to the axis of the central leg of the capillary; the amount of lateral offset of this beam, relative to the central leg of the capillary, at the point of incidence of the beam on the capillary; and the degree of collimation of this beam at the entrance elbow. Such optimization is measured by a performance parameter, such as the signal-to-noise ratio, the gain or some combination of these parameters produced by this detector cell.

In the preferred embodiment, the imaging system consists of one or more lenses, but in other embodiments, the imaging system can include one or more reflectors. This imaging system need not produce sharply defined images, such as are produced by telescopes and microscopes, but instead need only concentrate an incident beam of exposing light into the central leg. This ensures that a much larger fraction of the exposing light exposes the test solution. The degree of collimation of this incident beam should be such that most of the light rays within this beam do not escape through the outer wall of the central leg. The "degree of collimation" can be specified by several different measures, such as the maximum angular spread of any pair of rays in this beam or the minimum angular spread between a subset of rays that consist of some preselected percentage (e.g. 90%) of the rays in the incident imaged beam. The particular examples presented herein measure the degree of collimation in terms of the maximum angular spread between any pair of rays in the incident imaged beam.

Preferably, the degree of collimation is such that none of the rays in this beam escape through the outer wall of this central leg. An even greater efficiency is achieved by selecting these three parameters such that the beam of light is collimated within the central leg. Ideally, not only is this beam collimated within the central leg, it also fills the entire cross-section of the bore within the central leg.

Ideally, in the portion of the beam path within the bore of the central leg of the Z-Cell, the beam consists of a bundle of parallel rays that are parallel to and centered on the axis of the central leg of the Z-cell and that just fill the lateral cross-section of the capillary bore. If the lateral diameter of this beam were smaller than the diameter of the capillary bore, then only a portion of the sample would be exposed and that portion that is exposed would be much more likely to saturate, thereby reducing the output signal. This is generally not a problem, but can be in special circumstances. If the lateral diameter of this beam were larger than the bore, then those portions of the beam that lie outside of the bore would not only be ineffective in contributing to the signal, these portions would also degrade the signal-to-noise ratio by increasing the noise component of the output signal.

This relationship between the exposing light and the bore of the central leg of the Z-Cell ensures that the signal component will be much larger than is now achieved by the Z-Cell presented in the above-discussed reference by Chervet and that the noise component will be less than is now achieved using that Z-Cell. Because many capillaries have a bore diameter on the order of 50–100 microns, the incident beam of exposing light and the bore of such Z-Cells will both have diameters on the order of 50–100 microns, making it a difficult problem to image the light into the bore and parallel to the axis of the bore.

Although it is preferred that the beam be collimated within the capillary, some noncollimation (i.e., convergence or divergence) of the rays will not significantly change the signal-to-noise ratio if the amount of noncollimation is such that substantially all of these rays are totally internally reflected at the outer surface of the capillary where the index of refraction decreases substantially stepwise. This ensures that such rays are reflected back through the central bore of the capillary, so that such rays executed a zigzag path through the sample solution. The length of the portion of such zigzag path within the bore will typically be smaller than the length of the central bore, so that there will be some decrease in the signal component compared to that achieved when all of these rays are parallel to the axis of the bore, but the integral of the light intensity over the volume of the bore will still be much larger than now achieved with a Z-Cell.

In general, the imaging system cannot be arranged simply to produce a parallel beam of diameter equal to that of the bore of the Z-Cell capillary and aligned collinearly with the axis of the central leg of the Z-Cell, because the exposing light passes into the capillary through the curved entrance elbow, which affects both the direction and degree of collimation of the beam. It is therefore necessary to analyze the effect of the entrance elbow on the incident beam of exposing light.

In accordance with the present invention, the amount of offset and bending are determined (e.g., by ray modeling and/or empirically), so that a direction and alignment of the incident beam of exposing light is selected that maximizes the signal-to-noise ratio of the resulting detection system. This requires that lenses used to image this light onto the entrance elbow be offset from the axis of the central leg of the Z-Cell and be aligned along a direction with respect to the central axis of the central leg of the Z-Cell such that this imaged exposing beam of light is deflected by this bend along the central axis of the central leg of the Z-Cell. The direction of a central axis of the beam and/or the cone of divergence or convergence of the incident exposing light can be selected to maximize some performance parameter, such as the signal-to-noise ratio or the gain produced by this system.

The imaging system preferably utilizes one or more ball lenses, because the effect on the beam of such lenses is not affected by the rotational orientation of these lenses, thereby making such an imaging system easy to assemble and free of lens orientation misalignment that can be easily introduced using nonspherical optical elements. This imaging systems can therefore be assembled much more easily and quickly than one that does not utilize ball lenses and will be much more repeatable in its performance.

Such lenses are also advantageous, because this imaging system can utilize ball lenses having a diameter on the order of a few millimeters. This size is large enough to handle with ease and still produce a compact optical system. For ultraviolet (UV) light systems, such as are widely used in the analysis of organic chemicals, a particularly good choice is quartz ball lenses, because quartz has a high transmittance for UV light and because its index of refraction for such light enables one of the lenses to be placed in contact with or closely spaced from the outer wall of the capillary, thereby producing an imaging system that can be quickly and repeatably assembled. This ball lens is preferably press-fit into a central bore of a capillary/lens holder that holds this lens in contact with or adjacent to the outer wall of the capillary. This lens fixture also includes an aperture that is aligned with the central leg of the Z-Cell.

Description of the Figures

FIGS. 7A and 7B are front and side cross-sectional views of an embodiment adapted for fluorescence detection.

DESCRIPTION OF THE PREFERRED EMBODIMENT

Figure 1:
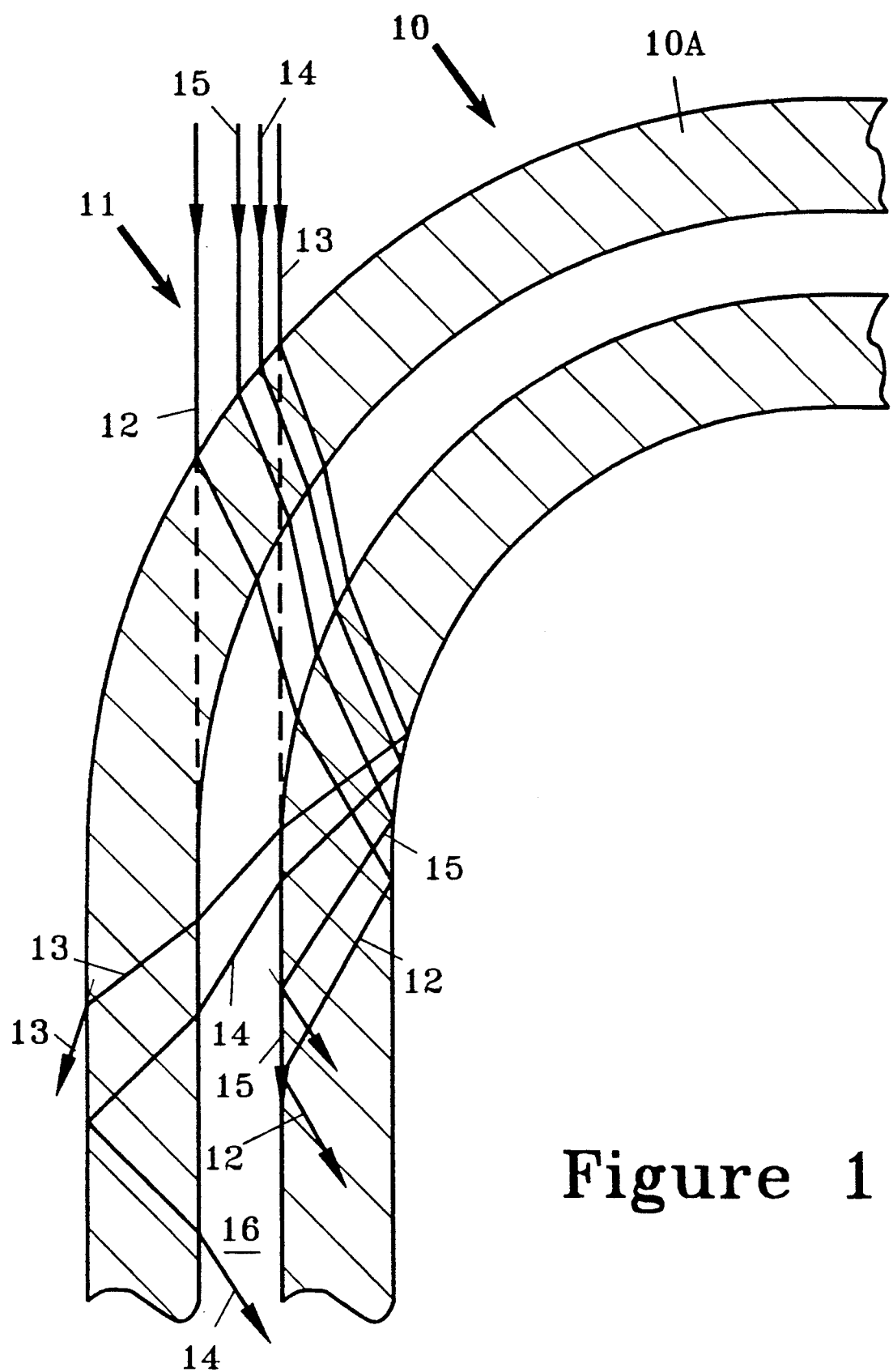
FIG. 1 is a side cross-sectional view of the entrance elbow of a Z-Cell for the case of an incident optical beam of exposing light that is collinear with the axis of the central leg of this Z-Cell and has a diameter equal to that of the bore of the central leg.
Figure 2:
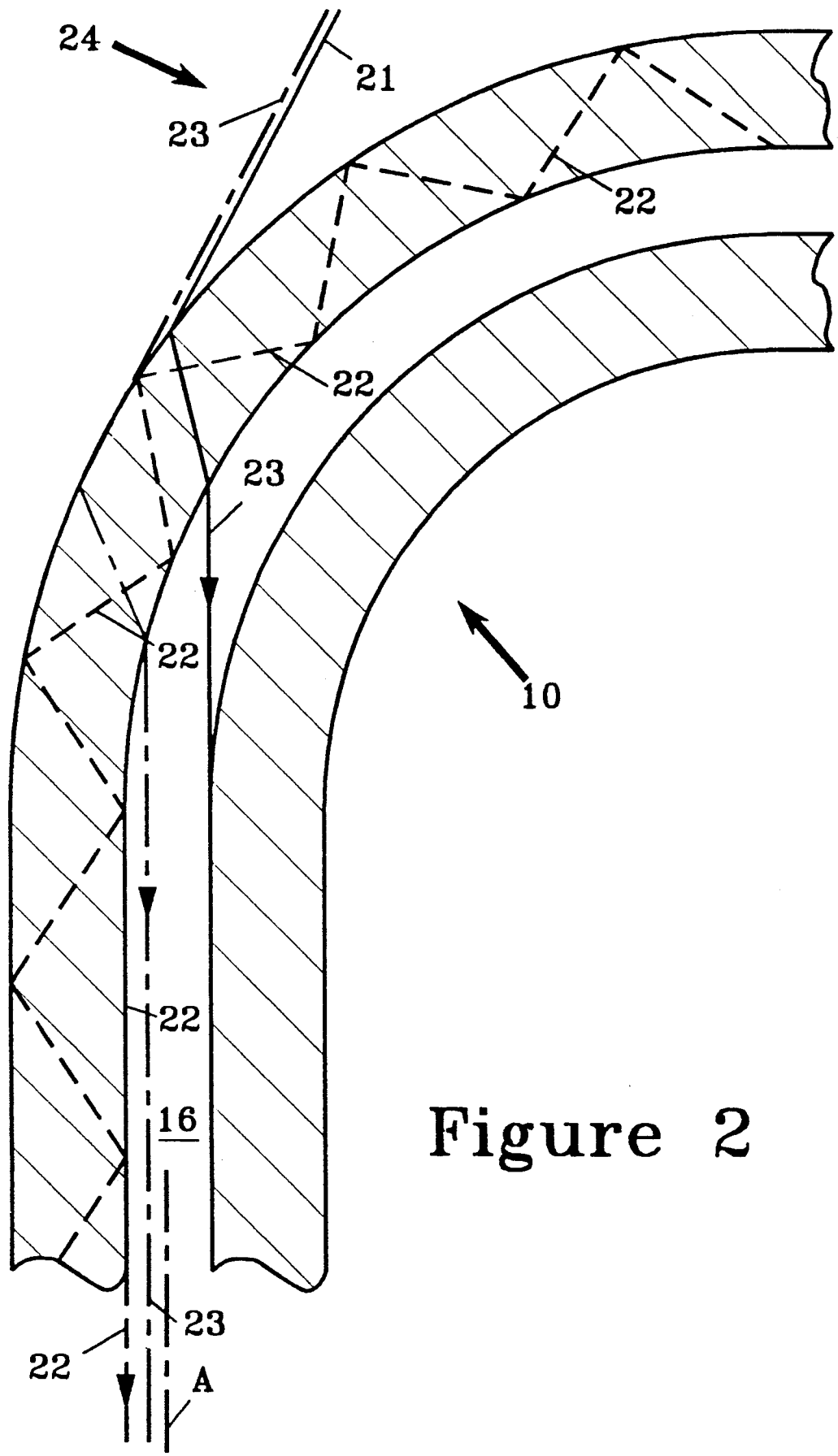
FIG. 2 is a side cross-sectional view of the entrance elbow of a Z-Cell illustrating a reverse ray tracing analysis to determine the direction and degree of collimation needed for the incident beam of exposing light to produce a beam of substantially parallel rays of diameter equal to that of the bore of the Z-Cell.
Figure 3:
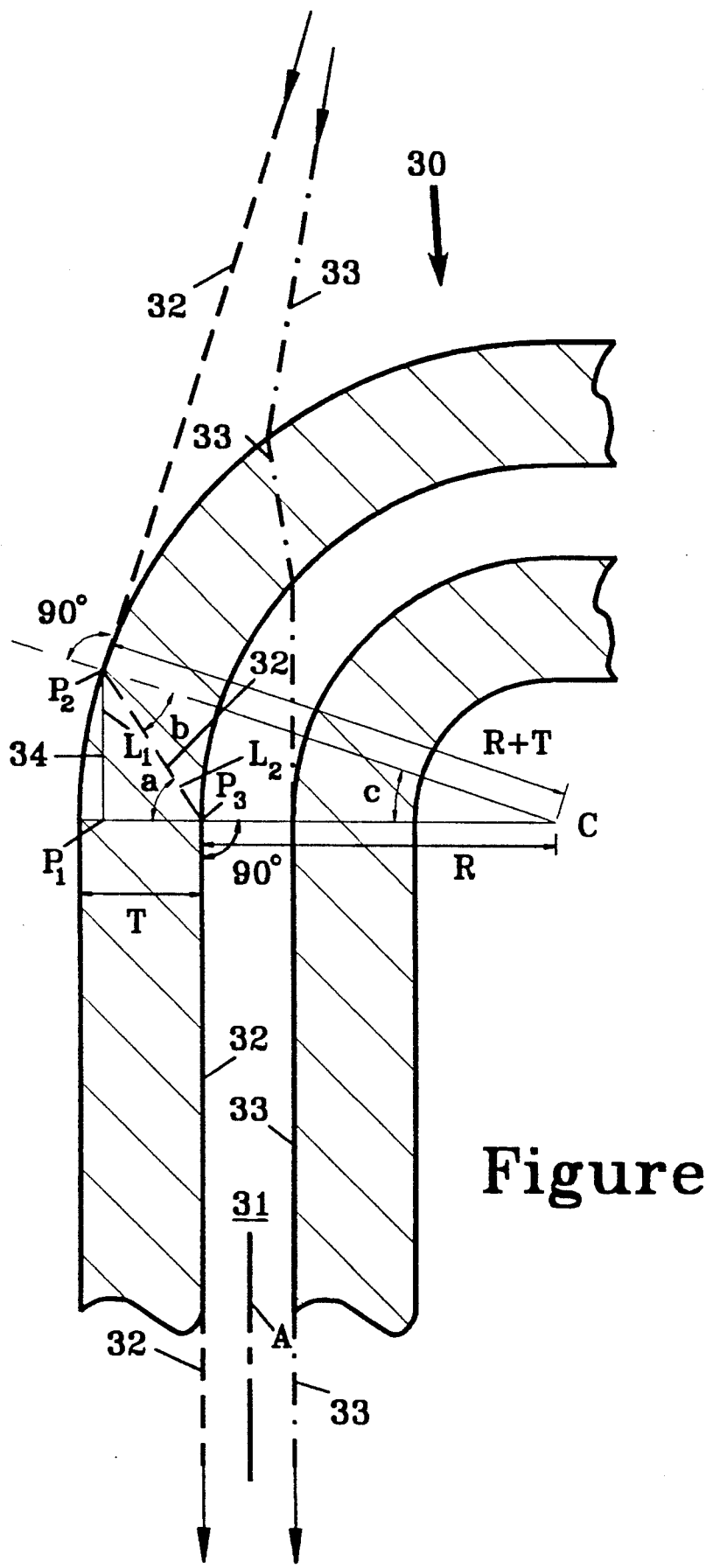
FIG. 3 illustrates the determination of the largest radius of curvature of the entrance elbow of a Z-cell that will enable a beam to be projected into the capillary bore in a manner that fills the central leg of the capillary with substantially parallel rays of light.

The ray traces presented in FIGS. 1–3 are all contained within a plane that contains a central axis of the Z-Cell. Therefore, the following remarks about the rays in an exposing beam of light actually apply only to rays within this plane. However, these rays illustrate the qualitative nature of all of the rays in the exposing beam of light, so that a more rigorous analysis will agree qualitatively with the following results for this subset of the rays in the incident beam.

FIG. 1 is a side cross-sectional view of the entrance elbow 10 of a Z-Cell capillary 10A for the case of an incident optical beam 11 of exposing light, that is incident on the Z-Cell along a path that is collinear with the axis of the central leg of this Z-Cell. The diameter of beam 11 is equal to the diameter of the bore 16 of the central leg. This choice of incident beam would concentrate all of this incident light into the capillary bore and would expose all of the fluid within the bore, if such beam were not deflected by the curved surfaces of the entrance elbow. Thus, FIG. 1 illustrates that a simple minded approach of imaging the exposing light to form a collimated beam collinear with the capillary bore and having a diameter equal to that of the capillary actually produces only a weak exposure of the sample solution within the central leg of the Z-Cell. As illustrated in this figure, such weak exposure results, because entrance elbow 10 of the Z-cell deflects the direction of the beam such that it would miss the bore of the capillary within this central leg, except for the reflection of some of the rays from the outer wall of the capillary such that some of these rays travel along a zigzag path that passes through the bore one or more times. Not only does this weak exposure of a sample reduce the signal portion of the output signal, it will also generally increase the noise component so that the performance of this system, as measured by the signal-to-noise ratio of this system, will be degraded both by the reduced signal component and the increased noise component of the system output signal.

In this figure, the effect of entrance elbow 10 on beam 11 of parallel rays is illustrated by the effect of this elbow on a set of rays 12-15 that exemplify the behavior of all of the rays in this beam. Because of the curvature of the capillary in the entrance elbow, all of the input rays are bent toward the right. For this particular elbow bend radius, rays 12 and 13 both pass through the core and experience complete internal reflection at the right hand outer surface of the capillary. Ray 13 escapes through the left hand outer surface of the capillary after passing a second time through the bore. Rays 12 and 15 get trapped within the wall and therefore each makes only a single short pass through the bore. Thus, rays 12, 13 and 15 each passes through the bore only over a distance much shorter than the length of the central leg of the Z-Cell. The efficiency of this exposure is therefore closer to that of conventional systems in which the exposing light is directed perpendicular to the axis of the capillary, instead of along this axis as is desired in a Z-Cell.

Rays closer to the center of the beam, such as ray 14 will zigzag back and forth through the bore, thereby producing a greater amount of absorption of this ray or inducing more fluorescent emission from the liquid in the capillary bore than will rays 12 and 13, but will still produce much less absorption or induce much less fluorescent emission than would a ray that remains within the bore over the entire length of the central leg of the Z-Cell. It is therefore preferred to select the lateral displacement and/or degree of collimation of incident beam 11 such that, within the capillary, a greater fraction of this beam of exposing light travels within the core of the central leg of the Z-Cell over substantially the entire length of the central leg of the Z-Cell.

Ray 15 is the ray that winds up, after one reflection off of the right outer surface of the capillary, being split such that a portion of this incident ray is directed parallel to the axis of the central leg along the rightmost edge of the bore. The reflected portion of this ray is substantially trapped within the capillary wall. Therefore, all of the rays between ray 15 and ray 12 are trapped within the wall of the capillary and therefore make only a single tilted pass through the bore of the capillary. Only those rays between and including rays 14 and 15 will make multiple passes through the capillary bore. Thus, only a small fraction of the rays in the incident beam of exposing light pass through the capillary bore within the central leg of the Z-Cell and the average length of passage through the bore is much less than the length of the central leg of the Z-Cell.

FIG. 1 indicates that, instead of starting with the incident rays and calculating the path of these rays through the capillary, it will be more productive to implement a reverse ray trace in which we start with the desired ray pattern within the capillary and trace such rays backward to determine what parameters of the input beam are needed to achieve the desired pattern of rays within the capillary.

FIG. 2 is a side cross-sectional view of the entrance elbow 10 of a Z-Cell illustrating such a reverse ray tracing analysis. As illustrated by ray 21, in order to direct a beam of light along the rightmost edge of bore 16, such an input ray must be directed along a path that angles downward to the left and is incident on the entrance elbow near the axis A of the central leg of the Z-Cell. However, when a reverse ray trace is made of the ray 22 that travels along the leftmost edge of bore 16, it is discovered that such ray bends into the wall of the Z-Cell and is trapped within that wall. Ray 23 is the leftmost ray within the bore that is parallel to axis A and that can be injected by an external ray incident on entrance elbow 10. This example shows that no beam exists that can be directed onto the entrance elbow to completely fill the bore of this capillary.

This example also shows that the incident beam 24 of exposing light for this Z-cell must be even narrower than the bore of the capillary and must be substantially collimated. Because such bore is typically very small (on the order of 50 microns), this demands a very narrow incident beam. As illustrated in FIG. 3, this problem and the problem of being unable to fill the bore with exposing light can be alleviated by use of a Z-Cell having a smaller radius of curvature, relative to its cross-sectional diameter, than that illustrated in FIG. 2. The actual radius required can be easily determined by ray trace analysis as presented in these FIGS. 1-3. FIG. 3 illustrates that the tighter bend of the entrance elbow 30 in that figure enables the entire bore to be filled with parallel or quasiparallel rays of exposing light and the input beam can have, at the entrance elbow, a diameter comparable to the diameter of the capillary bore (on the order of 50-100 microns).

For a capillary having a wall thickness T, the largest radius of curvature R of the leftmost edge of the capillary bore 31, that is consistent with filling the entire bore with exposing light, is calculated as follows. A leftmost ray 32 is tangent to the left edge of the capillary in the straight central leg of the Z-Cell and, at the boundary between the straight central leg and the curved entrance elbow 30 is refracted into the left portion of the capillary wall. The angle a therefore satisfies the condition:

$$n_w \sin(a) = n_L \qquad (1)$$

where $n_w$ is the index of refraction of the capillary wall and $n_L$ is the index of refraction of the liquid in bore 31. Typical values for $n_L$ and $n_w$ are 1.33 and 1.6, respectively.

The largest radius R of the elbow that is consistent with this requirement occurs when this backtraced ray is incident on the outer surface of the capillary wall at an angle b equal the critical angle at this outer wall. This requires that $$n_w \sin(b) = 1. \qquad (2)$$

The value of R consistent with this choice is determined as follows. By Euclidean geometry, the exterior angle a is related to the internal angles b and c by the relationship $$c = a - b. \quad (3)$$

From the geometry of triangles $P_1$-$P_2$-$P_3$ and C-$P_1$-$P_2$, the following relations also hold:

$$(R+T)\cdot\sin(c) = L_1 = L_2\cdot\sin(a) \quad (4)$$

and $$L_2\cdot\cos(a) + R = (R+T)\cdot\cos(c). \quad (5)$$

The parameters $n_w$ and T are determined by the choice of capillary. The parameter $n_L$ is determined by the choice of solution being tested, but will typically be substantially equal to 1.33. These three given values and the above 5 equations are sufficient to determine uniquely the minimum value R of the radius of curvature of the entrance elbow in terms of the other eight parameters $n_w$, $n_L$, a, b, c, T, $L_1$ and $L_2$.

FIG. 3 also illustrates that the incident beam of light that optimally illuminates the sample liquid within the central leg of the Z-Cell will generally not be parallel to the axis of the central leg of the Z-Cell and will generally be noncollimated. Although it is preferred to optimize the degree of collimation of the exposing light as well as the average direction of this light in order to maximize the performance parameter, in alternate embodiments only the degree of collimation of the exposing light is optimized for a preselected direction of the central axis of the exposing light or the direction of the central axis of the exposing light is optimized for a preselected degree of collimation. There are several choices for the performance parameter, including the signal-to-noise ratio of the output signal, the gain and the minimum detectable concentration.

The forward ray tracing approach utilized in FIG. 1 can also be utilized to optimize a selected parameter or set of parameters to optimize the performance parameter of the capillary cell. For example, for an incident beam of exposing light of preselected beam diameter, direction and degree of collimation, the ray traces can be evaluated for various choices of lateral offset of the beam to determine that offset that optimizes the performance parameter of the capillary cell.

Figure 5:
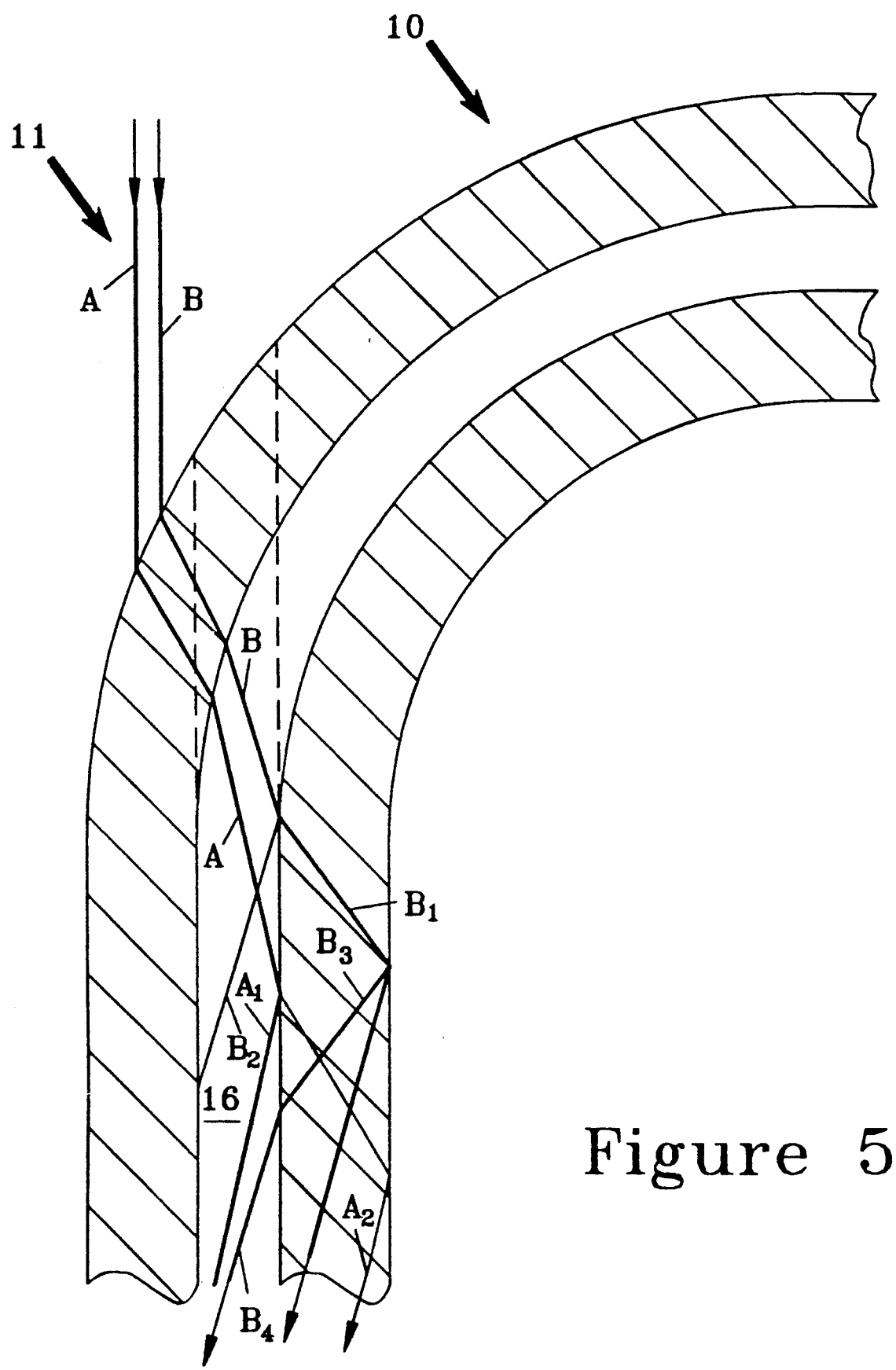
FIG. 5 illustrates the case of an input beam offset laterally to optimize performance and illustrates the effect of partial reflections at the various interfaces.

FIG. 5 illustrates the case of an input beam offset laterally to optimize performance. As illustrated in FIG. 1 for a pair of input rays A and B, the curvature of the entrance elbow deflects the beam toward the right, so that some improvement would be expected to occur if the input beam is shifted laterally to the left. This figure also illustrates that, at each interface, some of the ray incident thereon is transmitted through that interface and some of it is reflected. For a light ray incident on an interface from the side that has a lower index of refraction, the percent of the incident ray that is reflected is low until the angle of incidence is about 80° and then climbs steeply to 100% at 90° incidence. For a light ray incident on an interface from the side that has a higher index of refraction, the percent of incident ray that is reflected is low until the angle of incidence is within about 10° of the critical angle and then climbs steeply to 100% at the critical angle.

This splitting of the light is illustrated for ray B at two of the interfaces into rays $B_1$, $B_2$ and $B_3$. Those rays that, like ray $B_2$ travel within the sample, contribute to the sensitivity of the instrument. Thus, to the extent that rays can be directed within the capillary bore at an angle less than 10° from the capillary axis, a significant fraction of such rays will make multiple passes through the capillary bore, thereby contributing to an improved gain.

Figure 6:
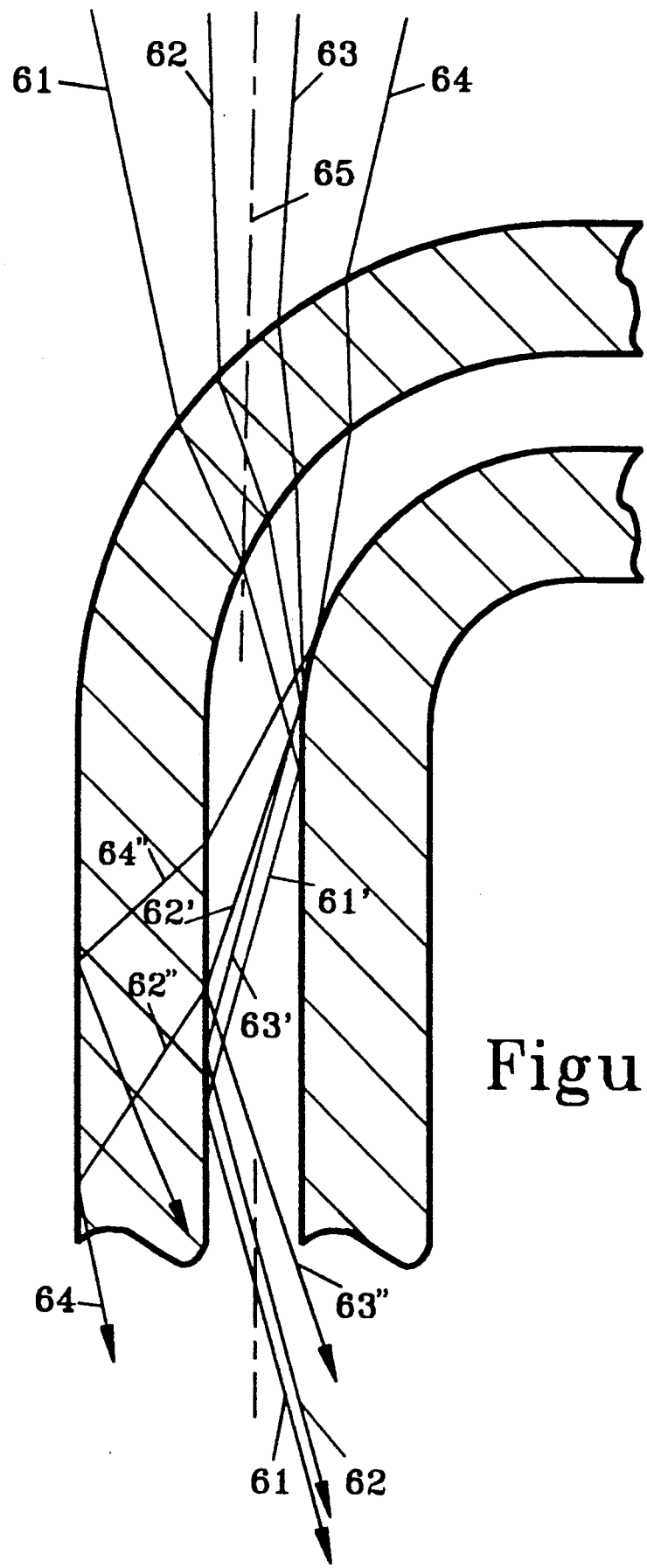
FIG. 6 illustrates the case of a noncollimated input beam.

FIG. 6 illustrates a set of incident rays 61–65 having a degree of collimation that has been selected to increase a performance parameter, such as the gain or the signal-to-noise ratio of the system. The rays in this figure exhibit angles of incidence on the right inner surface of the capillary wall of nearly 90° and therefore are very strongly reflected from that surface. Because the next incidence of these rays on the inner wall of the capillary is within the straight section of the capillary, this angle of incidence is also near to 90°. This produces a significant reflection from this wall (as illustrated by rays 61', 62' and 63') and illustrates the effect of partial reflections at the various interfaces. Rays 62" and 64" are representative of that portion of the light that is transmitted through the left inner surface of this wall. By means of numerical analysis or empirical measurements, the performance parameter can be optimized as a function of such degree of collimation.

Although this improved Z-cell is particularly well suited for absorbance measurements, it is also suitable for use in fluorescence measurements. Unfortunately, because the fluorescent light is emitted over the full length of the central leg of the Z-cell, additional optical elements are needed to collect this fluorescent light.

FIGS. 7A and 7B are front and side cross-sectional views of an embodiment adapted for detection of fluorescent light emitted from the central leg 71 of a Z-shaped capillary. Central leg 71 is located at a focal point of a first elliptical collector 72, so that substantially half of the fluorescent light emitted from central leg 71 is directed to an input end of a first optical fiber 73. This leg is also located at a focal point of a second elliptical collector 74 so that substantially all of the remaining half of the fluorescent light emitted from central leg 71 is directed to an input end of a second optical fiber 75. These fibers channel this emitted light to a detector that is therefore responsive to substantially all of the fluorescent light emitted from central leg 71. In an alternate embodiment, each fiber conducts the fluorescent light to an associated detector and the output signals from these two detectors are added. In another alternate embodiment, the two optical fibers are each replaced by a detector located to receive the light focussed through one of the foci of elliptical mirrors 72 and 74.

Figure 4A:
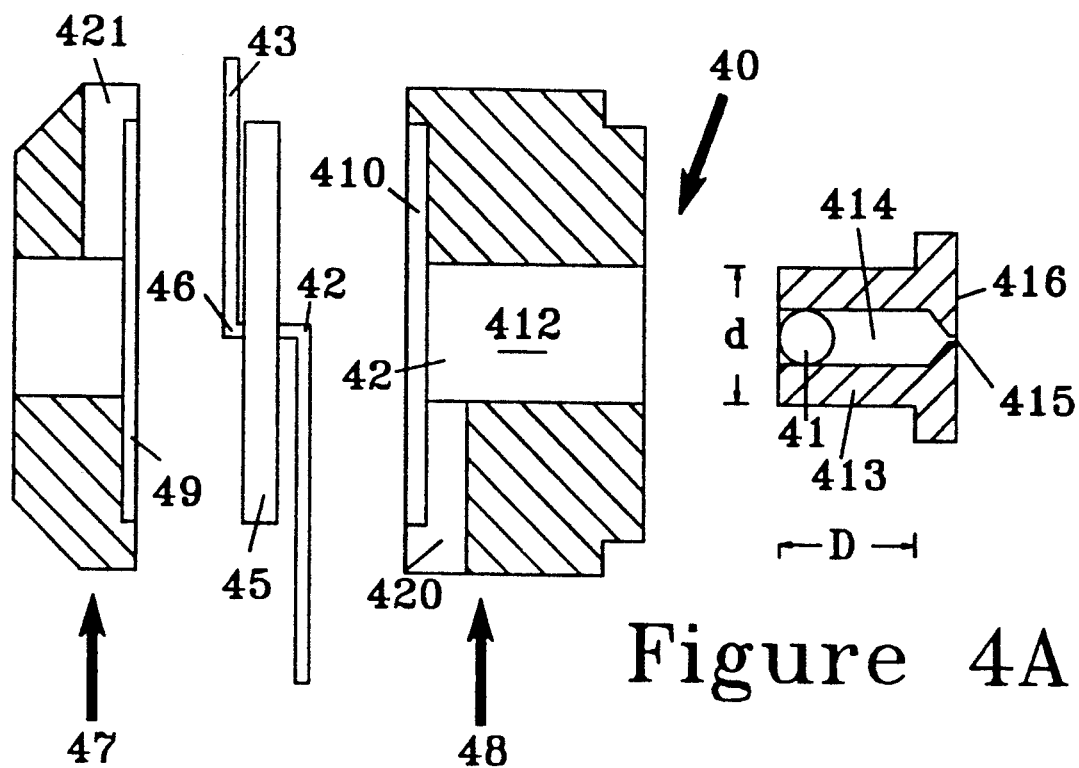
FIGS. 4A and 4B illustrate a capillary/lens holder that accurately aligns a ball lens with the entrance elbow of the Z-Cell.
Figure 4B:
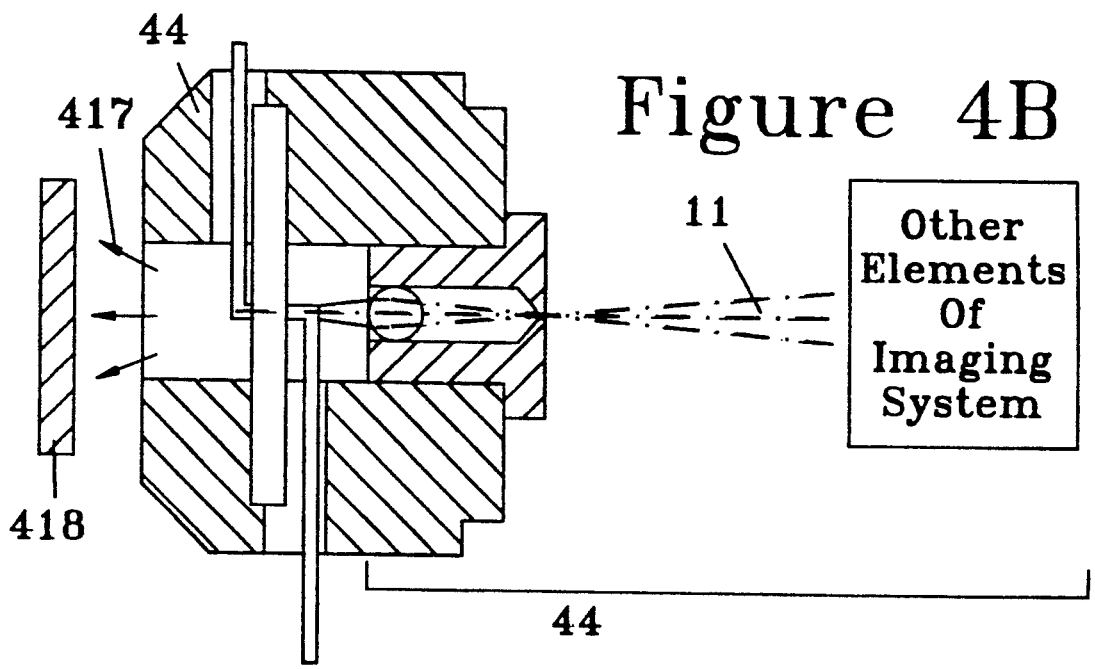
Figure 4C:
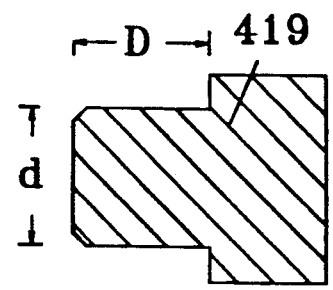
FIG. 4C illustrates a spacer tool used to accurately position the entrance elbow of the Z-Cell with respect to the incident beam.

Because of the small diameter of the bore (on the order of 50–100 microns) and of the outer wall of the capillary (on the order of 180–400 microns, it is important to align the optical elements accurately to achieve the necessary direction of the beam, the degree of collimation of the beam, the point of incidence of the beam onto the entrance elbow and the location of the detector with respect to the resulting output beam. FIGS. 4A and 4B illustrate a capillary/lens holder 40 that accurately aligns a ball lens 41 with an entrance elbow 42 of a Z-shaped capillary 43. This ball lens is part of an imaging system 44 (indicated in FIG. 4B) that images exposing light to form a beam 11 that is incident on the entrance elbow 42 of the capillary cell. Suitable choices of material for the ball lens include quartz and sapphire. Typical diameters of these ball lenses are on the order of 2–4 millimeters.

Capillary 43 is inserted through a central hole of a circular disk 45 and then is heated and bent to produce the entrance elbow 42 and an exit elbow 46. This central hole has a diameter just sufficiently larger than the outer diameter of the capillary that the capillary can easily be inserted through this central hole. Holder 40 consists of a pair of mating halves 47 and 48, in each of which is a circular recess 49 and 410, respectively, of diameter minimally larger than the diameter of disk 45 so that this disk can be readily inserted into such recesses while preserving accurate positioning of the entrance elbow within lens holder 40, thereby enabling this entrance elbow to be accurately positioned into an incident beam of light 11 as illustrated in FIG. 4B.

Holder mating half 48 includes a bore 412 into which can be snugly inserted a lens holder insert 413. This lens holder insert includes a cylindrical bore 414 of diameter slightly smaller than the diameter of ball lens 41. This insert is of a slightly compressible material, such as Delrin TM, so that the ball lens can be inserted into bore 412 and held snugly in place. This slight compressibility also enables this insert to be snugly inserted into bore 414 to accurately align the ball lens with entrance elbow 42 of the capillary. An aperture 415 in a top surface 416 functions as the entrance aperture for the incident beam of light 11 that is to be imaged through the bore of the central leg of the capillary. The resulting output light 417 from the central leg passes through a bore in mating half 47 to a detector 418.

In the preferred embodiment, the beam preferably converges in a cone of apex angle on the order of 30° to neckdown point adjacent to the entrance elbow, thereby enabling the desired diameter of the beam at the entrance elbow to be achieved. A 4 mm diameter ball lens is preferred, because it has a larger acceptance angle than a 2 mm ball lens. The ball lens is preferably quartz. Although sapphire ball lenses can be used, in embodiments using a sapphire ball lens, the neckdown point is inside of the ball lens, thereby making the placement of the ball lens more critical to performance than when the ball lens is quartz. The diameter of aperture 412 is on the order of 1.2–1.6 mm and the neckdown point is spaced from the entrance elbow by about 1 mm. For this choice, the beam diameter at the point of incidence on the entrance elbow is approximately equal to the 280 micron outside diameter of the entrance elbow.

To ensure accurate alignment of elements during assembly, a spacer tool 419 is used to position the entrance elbow accurately within lens holder 40. This spacer tool has a cylindrical portion having the same diameter d and depth D as the portion of the lens holder insert that fits within bore 412. This portion of the spacer tool is fully inserted into bore 412 and then circular disk 45 and capillary 43 are inserted into recess 410 and first capillary recess 420, such that the disk is fully inserted into recess 410 and the entrance elbow is brought into contact with the spacer tool. This accurately positions the entrance elbow within the lens holder. These items are glued together and then, after the glue has set, mating half 47 is fitted to and glued to mating half 48. A capillary recess 421 is included in mating half 47 to enable the capillary to fit within that element.

I claim:

1. A capillary detector cell comprising:
   a capillary having a central bore and an entrance elbow; and
   an imaging system that concentrates exposing light into an incident beam that is directed through the entrance elbow into a central leg of the capillary; wherein
   at least one of the following four parameters is selected to optimize a performance parameter, taking into account the effect of the entrance elbow of the capillary on the incident beam:
   (i) a diameter of the beam at a point of incidence of the beam onto the entrance elbow;
   (ii) a direction of this beam at this point of incidence;
   (iii) a lateral offset of this point of incidence relative to a central axis of the central leg of the capillary;
   (iv) a degree of collimation of the incident beam.

2. A capillary detector cell as in claim 1 wherein all of the rays of the incident beam strike the bore of the capillary within the central leg of the capillary.

3. A capillary detector cell as in claim 1 wherein the direction of the incident beam is such that the entrance elbow deflects a contiguous range of rays into the bore of the capillary within the central leg along a direction substantially parallel to a central axis of the bore in this central leg.

4. A capillary detector cell as in claim 1 wherein the degree of collimation of the incident beam is such that less than 20% of the rays that are directed into the central leg of the capillary exit through a sidewall of the central leg of the capillary.

5. A capillary detector cell as in claim 4 wherein the degree of collimation of the incident beam is such that substantially none of the rays that are directed into the central leg of the capillary exit through a sidewall of the central leg of the capillary.

6. A capillary detector cell as in claim 4 wherein the degree of collimation of the incident beam is such that substantially all of the rays that are directed into the central leg of the capillary traverse the full length of the central leg of the capillary within the bore of the central leg.

7. A capillary detector cell as in claim 6 wherein all of the rays that traverse the bore of the central leg of the capillary are parallel within the central leg.

8. A capillary detector cell as in claim 7 wherein the rays traversing the bore of the central leg of the capillary fill the bore within that region.

9. A capillary detector cell as in claim 1 wherein the rays traversing the bore of the central leg of the capillary fill the bore within that region.

10. A capillary detector cell as in claim 1 wherein a lateral offset of the incident beam is selected to optimize a performance parameter of the system.

11. A capillary detector cell as in claim 1 further comprising:
    a capillary/lens holder, in contact with at least one optical element of said imaging system and with the detector cell capillary to align accurately this imaging system with the entrance elbow of the capillary.

12. A capillary detector cell as in claim 11 wherein said optical element that is in contact with the capillary/lens holder is a ball lens.

13. A capillary detector cell as in claim 1 further comprising:

an elliptical collector having said capillary passing through an elliptical focal point of this collector; and a detector, responsive to light imaged by said first elliptical collector to a second elliptical focal point of this collector.

14. A capillary detector cell as in claim 1 further comprising:

a second elliptical collector having said capillary passing through an elliptical focal point of this collector; and a detector, responsive to light concentrated by said second elliptical collector onto this detector.

15. A method of optimizing performance of a detector cell that utilizes a capillary containing an entrance elbow through which an imaged beam of light is directed by an imaging system into a bore of a central leg of this detector cell, said method comprising the steps of:

(a) configuring the imaging system to accept exposing light and concentrate it onto the entrance elbow;

(b) determining the effect of the entrance elbow on rays of light in the imaged beam; and (c) optimizing a performance parameter of the detector cell by optimizing at least one of the following parameters:

(i) an diameter of the exposing light at a point of incidence of such light on the entrance elbow;

(ii) a direction of incidence of a central ray of this exposing light at said point of incidence;

(iii) a lateral offset of said central ray from an axis of the central leg of the detector cell;

(iv) a degree of collimation, at the point of incidence on the entrance elbow, of the incident beam of exposing light; and (v) a radius of curvature of the entrance elbow of the detector cell.

16. A method as in claim 15 wherein step (c) comprises selecting the diameter of the exposing light at the point of incident on the entrance elbow such that all of this incident beam of exposing light is incident on the bore of the capillary with the central leg of the capillary.

17. A method as in claim 15 wherein step (c) comprises selecting the direction of incidence of the central ray to maximize the signal-to-noise ratio exhibited by this detector cell.

18. A method as in claim 15 wherein step (c) comprises selecting the lateral offset of the central ray from the axis of the central leg to maximize the signal-to-noise ratio exhibited by this detector cell.

19. A method as in claim 15 wherein step (c) comprises selecting the degree of collimation of the incident beam of exposing light such that substantially all of this incident beam is directed into the central leg of the detector cell.

20. A method as in claim 18 wherein the degree of collimation is selected to direct all of the incident beam into the bore of the central leg of the detector cell.

21. A method as in claim 19 wherein the degree of collimation is selected such that the rays of exposing light, within the bore of the central leg, are parallel to a central axis of this central leg.

22. A method as in claim 19 wherein a radius of curvature of the entrance elbow is small enough that said parallel rays of exposing light in the bore of the central leg fill the bore of the central leg.

* * * * *